United States Patent
Pavlik et al.

(10) Patent No.: US 10,857,251 B2
(45) Date of Patent: Dec. 8, 2020

(54) PROCESS OF EMITTING OF HYDROGEN PEROXIDE VAPOR

(71) Applicants: Dusan Pavlik, Stary Jicin (CZ); Marek Kuzma, Plzen (CZ)

(72) Inventors: Dusan Pavlik, Stary Jicin (CZ); Marek Kuzma, Plzen (CZ)

( * ) Notice: Subject to any disclaimer, the term of this patent is extended or adjusted under 35 U.S.C. 154(b) by 0 days.

(21) Appl. No.: 16/096,323

(22) PCT Filed: Apr. 28, 2017

(86) PCT No.: PCT/CZ2017/000032
§ 371 (c)(1),
(2) Date: Oct. 25, 2018

(87) PCT Pub. No.: WO2017/186199
PCT Pub. Date: Nov. 2, 2017

(65) Prior Publication Data
US 2019/0125909 A1 May 2, 2019

(30) Foreign Application Priority Data
Apr. 29, 2016 (CZ) .............................. PV 2016-249

(51) Int. Cl.
*A61L 2/20* (2006.01)
*C01B 15/01* (2006.01)
*A61L 9/04* (2006.01)
*A61L 9/02* (2006.01)

(52) U.S. Cl.
CPC ............... *A61L 2/208* (2013.01); *A61L 9/02* (2013.01); *A61L 9/04* (2013.01); *C01B 15/01* (2013.01); *A61L 2202/11* (2013.01); *A61L 2209/211* (2013.01)

(58) Field of Classification Search
CPC ....................................................... A61L 9/04
See application file for complete search history.

(56) References Cited

U.S. PATENT DOCUMENTS

| | | | | |
|---|---|---|---|---|
| 2,657,753 A | * | 11/1953 | Carpenter | E21B 37/00 166/302 |
| 2,721,788 A | * | 10/1955 | Schad | C01B 13/0214 422/631 |
| 8,899,556 B2 | * | 12/2014 | Love | C01B 15/01 261/74 |
| 2005/0074359 A1 | | 4/2005 | Krieger et al. | |
| 2005/0084415 A1 | | 4/2005 | McVey et al. | |
| 2005/0230376 A1 | * | 10/2005 | Gomez | A61F 7/0085 219/385 |
| 2005/0234295 A1 | * | 10/2005 | Gomez | A61B 1/00142 600/121 |
| 2005/0252274 A1 | * | 11/2005 | Centanni | G01N 33/0036 73/23.2 |
| 2014/0256540 A1 | | 9/2014 | Sambandan et al. | |
| 2014/0294670 A1 | * | 10/2014 | Wiget | A61L 2/26 422/33 |

FOREIGN PATENT DOCUMENTS

WO WO 2007/008205 A1 1/2007

OTHER PUBLICATIONS

International Search Report dated Aug. 25, 2017 in corresponding PCT International Application No. PCT/CZ2017/000032.
Written Opinion dated Aug. 25, 2017 in corresponding PCT International Application No. PCT/CZ2017/000032.

* cited by examiner

*Primary Examiner* — Melissa S Swain
(74) *Attorney, Agent, or Firm* — Ostrolenk Faber LLP

(57) ABSTRACT

Method of emitting peroxide vapors or mixtures thereof, where the hydrogen peroxide is placed into a vessel, whereupon an initiator, catalyst or their precursor—ferrocene is added, from which the initiator or catalyst is created by reaction with peroxide or peroxide mixture.

10 Claims, No Drawings

PROCESS OF EMITTING OF HYDROGEN PEROXIDE VAPOR

CROSS-REFERENCE TO RELATED APPLICATIONS

The present application is a 35 U.S.C. §§ 371 national phase conversion of PCT/CZ2017/000032, filed Apr. 28, 2017, which claims priority to Czech Patent Application No. PV 2016-249, filed Apr. 29, 2016, the contents of which are incorporated herein by reference. The PCT International Application was published in the English language.

TECHNICAL FIELD

The invention relates to generation of vapors for the need of decontamination by gaseous media.

STATE OF THE ART

Various medias are currently used for the need of gaseous decontamination for decontamination purposes: chlorine dioxide, hydrogen peroxide, formaldehyde, oxirane, methylbromide and others. Some medias are used directly in the gaseous state—methyl, bromide, oxirane, some are generated directly before use—chlorine dioxide, further various methods of evaporating are being used for longer period of time—hydrogen peroxide, formaldehyde.

There is a wide range of apparatus used for evaporation. Such devices are known, for example, from documents WO2007/008205, US2005/0074359 or US2005/0084415. However, there is always a large number of parts and complicated manipulation common to these solutions where both require connection to the media as power, compressed air, etc., and the vapor emission is single for one performance.

The aim of present invention is to provide a method of emitting hydrogen peroxide which would be simple, efficient, without need of any energy connection, and which would be able to replace the other used methods of gaseous decontamination.

SUMMARY OF THE INVENTION

The aforementioned drawbacks are largely eliminated by the method of hydrogen peroxide vapor emitting according to the invention, whose principle lies in placing hydrogen peroxide into a vessel, whereupon an initiator, catalyst or their precursor—ferrocene is added, from which the initiator or catalyst is created by reaction with peroxide or peroxide mixture.

In a preferred embodiment is the initiator, catalyst or the precursor selected from the group of metals such as silver, gold, platinum, palladium; metal oxides such as manganese, silver, aluminum, iron; Metal salts such as manganese, aluminum, iron, silver; Organometallics, manganese, iron, aluminum—e.g. ferrocene or metal-containing mixtures such as iron, aluminum, manganese, silver or their compounds.

In another preferred embodiment the peroxide is used in the range of concentration between 10-90% and the temperature of usability of given configuration is from −10 to 100° C.

In another preferred embodiment for long-term exposure by decontaminating vapors, the process is repeated with a new charge of peroxide, or mixture and by adding of a new source of initiator or catalyst.

In another preferred embodiment the peroxide mixture is a peroxide mixed with one or more substances such as peroxyacetic acid, peroxyformate acid, formic acid, boric acid, phosphoric acid, organic or inorganic carbonates, N oxides, alcohols such as tert-butyl alcohol, amines, esters; monosylic, dibasic or tribasic carboxylic acids such as oxalic acid, acetic acid, citric acid, malic acid, tartaric acid, complexing agents such as chelatones, Komlexon I, II, III, the transition metal salts catalyzing the Fenton reaction, such as salts of iron, copper, silver, manganese and zinc.

In another preferred embodiment the emissions of the vapors is carried out directly in the treated space, or the vapors are brought through the pipeline route to the required destination.

In another preferred embodiment the gases or vapors emitted are diluted with another gas.

EMBODIMENTS OF THE INVENTION

The principle of the vapor emitting method according to the present invention allows to evaporate hydrogen peroxide vapors or mixtures with hydrogen peroxide. These vapors are subsequently used for decontamination purposes. This evaporation is achieved so, that a solution of hydrogen peroxide or mixtures thereof, are mixed with an initiator, catalyst, or catalyst source. After mixing with an initiator, catalyst, or source thereof, there occurs an initiating reaction or a catalytic decomposition, or a catalyst is formed which initiates the decomposition of peroxide. By the decomposition of peroxide, which is an exothermic reaction, and due to the stormy process of decomposition, there is evaporation of the peroxide or mixture, along with the emission of peroxide droplets or its mixtures. This process emits vapors and droplets of evaporated peroxide or mixtures, which appears under normal conditions as a smoke or steam. The resulting mixture is generated directly in the decontamination area, or is transported to the place of decontamination by pipeline. This smoke/steam contains peroxide or optionally a mixture thereof, in sufficient quantities for gaseous decontamination purposes. During the decontamination process the smoke/steam can be completely evaporated due to physical conditions, then the decontamination proceeds outside the condensation area. If there is no complete evaporation of smoke/steam due to the physical conditions, decontamination is happening in the area of condensation of used vapors. Generated vapors can be mixed with another gas for adjustment of required process parameters. The evaporation of the peroxide mixture with other substances provides greater chemical reactivity, which makes biological or chemical decontamination easier.

The vapor emitting method according to the present invention allows to generate vapors for decontamination without connecting to sources of energy and media. For the emmission of the vapors it is necessary to mix only hydrogen peroxide or mixture thereof and initiator, catalyst, or their precursor.

The subject of protection is the process of generating peroxide vapors or mixtures thereof, which replaces other methods used for gaseous decontamination purposes. The vapor emission occurs due to the catalytic or otherwise initiated decomposition of hydrogen peroxide.

EXAMPLE 1

12 ml of 69% hydrogen peroxide are metered into the vessel and the vessel is placed in the target space of 500 liters volume. 0.5 g of ferrocene is added to the surface of peroxide in the vessel. After the initial delay occurs a reaction when the ferrocene is burnt and decomposed which results in a decomposition catalyst and by higher temperature a catalytic decomposition is initiated. This reaction emits fumes of peroxide vapors that are used for decontamination.

EXAMPLE 2

To a 30 liters volume tin canister is metered 10 liters of 69% hydrogen peroxide, the vessel is placed in a target area with volume of 500 m$^3$. 120 g of ferrocen is poured into the vessel. After the initial delay occurs the burning and decomposition of ferrocene, thereby creating a catalyst of decomposition and higher temperature starts the catalytic decomposition. This reaction emits smoke of peroxide vapors or mixtures to be used in decontamination.

The invention claimed is:

1. A decontamination method comprising:
    emitting hydrogen peroxide vapor or a mixture having hydrogen peroxide vapor therein by placing hydrogen peroxide or a mixture containing hydrogen peroxide in a vessel;
    generating an exothermic reaction by adding an initiator, to the hydrogen peroxide in the vessel or the mixture containing hydrogen peroxide in the vessel, some of the hydrogen peroxide being decomposed in the exothermic reaction; and undecomposed hydrogen peroxide being vaporized by heat from the exothermic reaction; and
    providing the vaporized hydrogen peroxide or a mixture containing vaporized hydrogen peroxide resulting from the exothermic reaction to a contaminated space, wherein ferrocene is the initiator added to initiate the exothermic reaction.

2. The decontamination method according to claim 1, wherein the mixture containing hydrogen peroxide includes 10-90% and is usable in the temperature range −10 to 100° C.

3. The decontamination method according to claim 1, further comprising adding additional hydrogen peroxide or a mixture containing hydrogen peroxide to the vessel and adding additional initiator or catalyst to continue emitting the hydrogen peroxide vapor or the mixture having hydrogen peroxide vapor.

4. The decontamination method according to claim 1, wherein the mixture containing hydrogen peroxide includes at least one other chemical from a group of chemicals consisting of a peroxyacetic acid, a peroxyformate acid, a formic acid, a boric acid, a phosphoric acid, an organic carbonate, an inorganic carbonate, an N oxide, an alcohol, an amine, an ester, a monosilicic acid, a dibasic acid, a carboxylic acid, a tribasic carboxylic acid, a complexing agent, and a transition metal salt catalyzing a Fenton reaction.

5. The decontamination method according to claim 1, wherein the emitting is carried out directly in the contaminated space, or the emitted vapors are brought through a pipeline to the contaminated space.

6. The decontamination method according to claim 1, further comprising diluting the emitted hydrogen peroxide vapor or the mixture having hydrogen peroxide vapor with another gas.

7. The decontamination method of claim 1, wherein the mixture containing hydrogen peroxide includes tert-butyl alcohol.

8. The decontamination method of claim 1, wherein the mixture containing hydrogen peroxide includes an acid from a group of acids consisting of oxalic acid, acetic acid, citric acid, malic acid, and tartaric acid.

9. The decontamination method of claim 1, wherein the mixture containing hydrogen peroxide includes a complexing agent.

10. The decontamination method of claim 1, wherein the initiator, is added to the surface of the hydrogen peroxide or the mixture containing hydrogen peroxide in the vessel.

\* \* \* \* \*